United States Patent [19]

Leginus

[11] Patent Number: 5,367,061
[45] Date of Patent: Nov. 22, 1994

[54] METHOD OF DETECTING NITRATE ESTERS

[75] Inventor: Joseph M. Leginus, Silver Spring, Md.

[73] Assignee: Westinghouse Electric Company, Pittsburgh, Pa.

[21] Appl. No.: 57,386

[22] Filed: May 6, 1993

[51] Int. Cl.$^5$ .............................................. C07K 13/00
[52] U.S. Cl. .................................... 530/405; 435/7.93; 435/7.95; 436/815; 530/389.8
[58] Field of Search ................................ 530/403–407; 436/815; 435/7.92–7.95

[56] References Cited

FOREIGN PATENT DOCUMENTS 1012266  1/1989  Japan .
3274461 12/1991  Japan .

OTHER PUBLICATIONS

P. Tijssen, Practice and Theory of Enzyme Immunoassays, pp. 249–251, 279–287, Elsevier, N.Y. (1985).
B. Erlanger, Pharmacol. Revs., vol. 25, No. 2 (1973) pp. 271–280.

*Primary Examiner*—Mary E. Ceperley

[57] ABSTRACT

A method of detecting the presence and amount of a nitrate ester of a polyol in an unknown comprises preparing an antigen based on such an ester and using that antigen to raise antibodies for use in a biochemical assay for the nitrate ester. A preferred antigen is pentaerythritol trinitrate bonded to a protein such as thyroglobulin or BSA. Antibodies can be raised against this antigen in rabbits or other normally used laboratory animals, and the antibodies are used in, for example, a competitive inhibition enzyme immunosorbent assay (CIEIA).

4 Claims, 1 Drawing Sheet

METHOD OF DETECTING NITRATE ESTERS

BACKGROUND OF THE INVENTION

This invention relates to a new and improved method of detecting and identifying nitrate esters of polyhydric alcohols. In a specific embodiment it relates to the detection of nitrate ester-based explosives.

BACKGROUND OF THE INVENTION

At airports and in public buildings throughout the world the threat of bombings by terrorist organizations is very real. Since the explosives used by such people are normally either pentaerythritol tetranitrate (PETN) or nitroglycerine (NG), it is highly desirable to be able to detect these explosives. In forensic work also, such as the investigation of mysterious and suspicious blasts, and in solving certain shootings it is also desirable to be able to detect the presence of these explosives.

A variety of methods have been developed which can identify small quantities of explosive substances. These include chromatographic analyses, both gas and liquid, spectroscopic analyses, such as NMR and mass spectrometry, and, in an extreme case, sniffing dogs. It is the object of the present invention to provide an additional method of detecting these explosives as well as other nitrate esters of polyhydric alcohols. The present invention accomplishes this objective by using biological receptors to identify nitrate esters, using a procedure known as immunoassay.

SUMMARY OF THE INVENTION

This invention provides a method of detecting nitrate esters of low molecular weight polyhydric alcohols having a molecular weight of about 1,000 or less, preferably 400 or less, which method comprises immunizing a warm blooded mammal with an antigen comprised of a nitrate ester of a polyhydric alcohol coupled to a carrier protein, isolating nitrate ester-specific antibodies from the host mammal and employing said antibodies to detect the presence of nitrate esters via a biochemical assay. The invention also provides a new antigen comprised of a nitrate ester of a polyhydric alcohol coupled to a carrier protein.

DETAILED DESCRIPTION OF THE INVENTION

Figure 1:
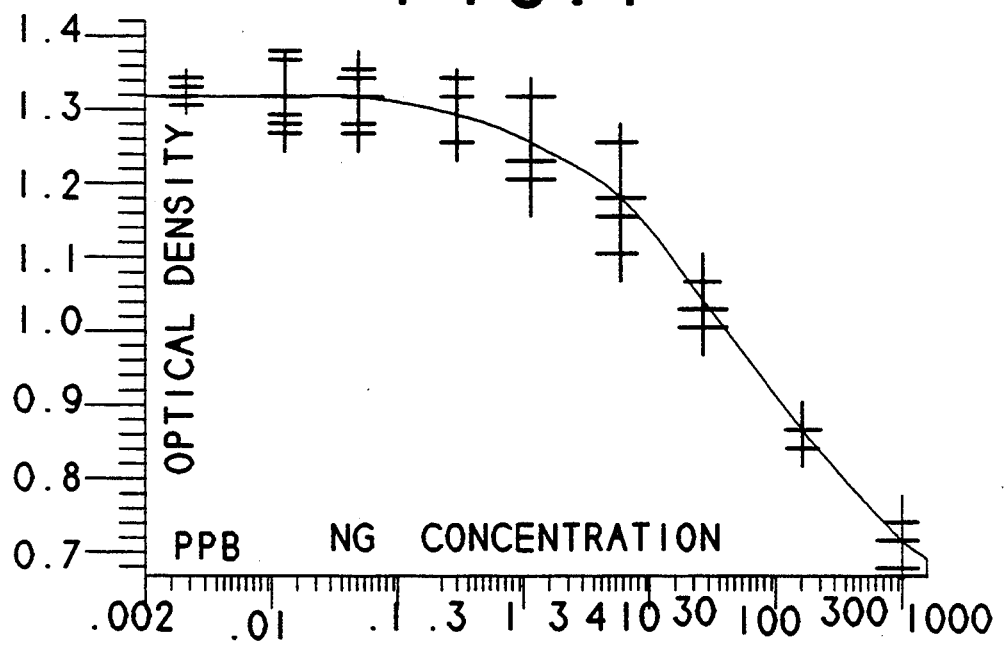
FIG. 1 is a computer generated curve showing optical density of a solution of tetramethyl benzidine in the presence of various concentrations of nitroglycerin.

To detect the presence of nitrate esters using the method of this invention, an effective amount of an antigen (antibody generator) comprised of a nitrate ester attached to a carrier protein is injected into a warm blooded mammal thereby inducing the formation of antibodies by the host mammal. These antibodies are then collected and used as the reagent for detecting the presence of the nitrate esters in other environments.

The relatively small nitrate ester compound is not capable of inducing an immune response and thus must be chemically attached to a protein molecule having a molecular weight of at least about 10,000 to form the antigen.

There is no upper limit to the molecular weight of the protein. Typical proteins that can be employed include bovine serum albumin (BSA), thyroglobulin, keyhole limpet hemocyanin (KLH) and ovalbumin.

Coupling of the nitrate ester to the protein can be accomplished with any relatively low molecular weight difunctional compound having a functional group or groups reactive with both the nitrate ester and the protein. Preferably, the coupling is accomplished with a 4 to 10 carbon dicarboxylic acid which esterifies one hydroxyl group of the polyhydric alcohol and bonds to the protein via a peptide linkage.

The preferred nitrate ester for preparing the antigen is pentaerythritol trinitrate which has three of the four pentaerythritol hydroxyl groups nitrated, leaving one hydroxyl free for the attachment of the alkyl carboxy linking group. Dinitroglycerine can also be used to prepare the antigen as it also has a free hydroxyl group for attachment to the protein.

The nitrate ester used in preparing the antigen need not be the same ester as would be present in an unknown to be tested using the method of the invention. For example, an antigen prepared by use of pentaerythritol trinitrate can be used to detect the presence of other, structurally related nitrate esters as well. Thus, such an antigen can be used to detect the presence of, e.g. PETN, NG, dinitroglycerine, ethylene glycol dinitrate, propyiene glycol dinitrate or even pentaerythritol di- or tri-nitrate and the like.

While the method is effective for detecting nitrate esters in general, it is particularly effective for detecting esters that have a series of 2 or more nitrate groups on adjacent carbon atoms in a linear structure. Since an antibody recognizes the three dimensional shape of the molecule it was raised against, the antibody raised against pentaerythritol trinitrate readily recognizes such structurally related compounds.

The antigen, in a suitable carrier, in particular, a saline solution, is injected into a host warm blooded mammal to induce formation of nitrate ester-specific antibodies in the serum of the host mammal. Injections of an amount of the antigen sufficient to trigger an immune response, with formation of antibodies, are given repeatedly at approximately 4 week intervals over a 3 to 6 month period. Samples of the animal's blood are collected 5 to 7 days after each injection and serum, containing antibodies, is isolated from the blood and centrifuged to remove solid matter. Although any warm-blooded mammal will produce antibodies, preferred host animals include mice, rabbits and other animals normally employed in laboratory work.

Antibodies harvested from the host animal's blood are then used as the reagent in a biochemical assay which detects the presence of the nitrate esters in an unknown. Antibodies can be used as they are harvested, i.e. so-called polyclonal antibodies, or monoclonal antibodies can be prepared by an alternative method and can also be used.

A preferred biochemical assay is the so-called competitive inhibition enzyme immunosorbent assay (CIEIA). Other biochemical assay methods such as enzyme linked immunological assay and radioimmunological assay can also be used.

In the CIEIA technique, a solid support, typically a conventional multi-well microtiter plate, is coated with the antigen, which adheres to the well surfaces. A competitive inhibition reaction occurs when a specimen containing the nitrate ester and the antibody raised against the nitrate ester are brought into contact with the antigen-coated support. A competition for antibodies is established between the free nitrate ester in solution and the nitrate ester-based antigen bound to the surface of the microtiter plate. After about one hour or less, the liquid phase is removed and the plate is rinsed with phosphate-buffered saline (PBS) solution leaving behind only the antibodies that have adhered to the support. At this point, there is added an enzyme-antibody complex based on an antibody from an animal different from that from which the antibody bound to the antigen coated on the support was obtained. This complex bonds directly to the bound antibody. Typical enzymes useful for such complexes include horse-radish peroxidase and alkaline phosphatase.

After a suitable time for the reaction to be completed, typically no more than one hour, any unreacted (i.e. unbound) enzyme-antibody complex is removed and a solution of an enzyme substrate is added. The enzyme substrate reacts with the bound enzyme-protein complex to form a colored product, the amount of color formed being directly proportional to the amount of surface bound antibody and, thus, inversely proportional to the amount of nitrate ester in the specimen.

The presence of nitrate esters and the amount in the specimen can then be determined by comparing the color against a previously prepared calibration curve prepared by carrying out the above procedure with known amounts of nitrate ester and plotting nitrate ester concentration against optical density. Optical density readings are made with a spectrophotometer.

The invention will be illustrated by the following example, which is not intended to be limiting except as the invention may be limited by the appended claims.

EXAMPLE

Chemical Synthesis of Antigens

Pentaerythritol (8 grams, 0.06 mol) was stirred in 40 ml (0.28 mol) of acetic anhydride and 250 mg of 4-dimethylamino-pyridine at 100° C. for one hour. The solution was poured into ice water, yielding a white precipitate which was filtered, washed with water and dried. The precipitate was recrystallized from hexane, yielding 11.8 grams (65% yield) of pentaerythritol tetraacetate as colorless needles (mp 76°–77° C.).

Pentaerythritol (9.5 grams, 0.07 mol), 7.0 grams (0.02 mol) of pentaerythritol tetraacetate and 500 mg of potassium carbonate were heated for 12 hours at 180° C. A light brown solution resulted which was boiled for 15 minutes in 50 ml of acetone and the resulting precipitate was filtered off. The filtrate was concentrated and passed through a plug of silica gel using acetone as a solvent. The mixture was purified by flash chromatography (1:1, $CHCl_3$:acetone) to yield a product of $R_f=0.1$. Addition of 25 ml of ether caused the product to solidify, yielding 4.6 grams of pentaerythritol monoacetate as a white solid.

Pentaerythritol monoacetate (4.6 grams, 0.03 mol) was slowly added to 15 ml of fuming nitric acid at 0° C. After stirring for 2 hours at 0° C., the solution was poured into ice water and stirred for 15 minutes, at which time the solid precipitate was filtered off. The precipitate was washed with water and air dried, then crystallized from ethanol yielding 5.8 grams of pentaerythritol acetate trinitrate.

Pentaerythritol acetate trinitrate (2.0 grams, 0.006 mol) was dissolved in 20 ml of acetone and added to a solution of 332 mg of NaOH dissolved in 10 ml of water. To this mass was added 5 ml of ethanol to effect solution. The solution was stirred at room temperature for 30 minutes whereupon 1N HCl was added to bring the pH of the solution to approximately 7. The volatiles were removed under vacuum and the remaining liquid was extracted twice with ether. The combined ether extracts were washed with brine and concentrated. The mixture was purified by flash chromatography (1:1, ether:hexane) to isolate a product of $R_f=0.5$. About 1.1 gram of pentaerythritol trinitrate was isolated as a colorless oil.

Pentaerythritol trinitrate (0.8 gram, 0.003 mol) was combined with 0.4 gram (0.03 mol) of glutaric anhydride and 50 mg of 4-dimethylamino pyridine in 25 ml of ether. The mixture was stirred at boiling for 12 hours and concentrated under vacuum, then the oily residue was partitioned between ether and saturated $NaHCO_3$. The aqueous base layer was removed and acidified with 1N HCl to approximately pH 6. The solution was cooled in ice and after 15 minutes a white precipitate was collected, washed with water and air dried, yielding 0.5 gram of pentaerythritol trinitrate glutarate in the form of a white powder.

Ten (10) mg of pentaerythritol trinitrate glutarate was dissolved in 5 ml of dioxane. To this was added 12 mg of tri-n-butylamine and 8 mg of isobutyl chloroformate. The mixture was stirred for 45 minutes and was identified as mixture A.

To a premixed solution of 100 mg of Bovine Serum Albumin (BSA) dissolved in two ml of water, 0.1 ml of 1N NaOH and 1 ml of dioxane at 0° C. was added 2 ml of mixture A. This solution was stirred at 0° C. for 1 hour and then for 1 hour at room temperature. The solution was then transferred into dialysis membrane tubing (Spectrapor, m.w. cutoff: 6,000–8,000) and dialyzed against deionized water for 25 hours (two changes of water). The solution was removed from the dialysis tubing, frozen and lyophilized to produce 105 mg of PETN-BSA antigen.

To a premixed solution of 100 mg of porcine Thyroglobulin dissolved in 2 ml of water, 0.1 ml of 1N NaOH and 1 ml of dioxane at 0° C. was added 3 ml of mixture A. This mixture was dialyzed and lyophilized as in the preceding paragraph, yielding 92 mg of PETN-thyroglobulin antigen.

Preparation of Antibody

One (1) mg of each antigen was separately dissolved in 1 ml of phosphate-buffered saline solution of pH 7.4 and emulsified with 1 ml of complete Freund's Adjuvant (a water-in-oil emulsion prepared from nonmetabolizable oils and containing killed M. tuberculosis bacteria).

Two sets of two rabbits of the New Zealand albino strain were immunized sub-cutaneously with 0.4 mg of antigen, one set with PETN-BSA and one set with PETN-thyroglobulin. A booster injection of 100 micrograms of antigen in buffer and adjuvant were given every 4 weeks for 6 months. Blood containing antibodies was collected from each rabbit by ear vein bleed 5 to 7 days after each booster injection without sacrificing the rabbits. After collection, the blood was allowed to clot for 60 minutes at 37° C., the clot was removed, and any remaining insoluble material was removed by centrifugation at 10,000 G for 10 minutes at 4° C. The serum was stored at −70° C.

Figure 2:
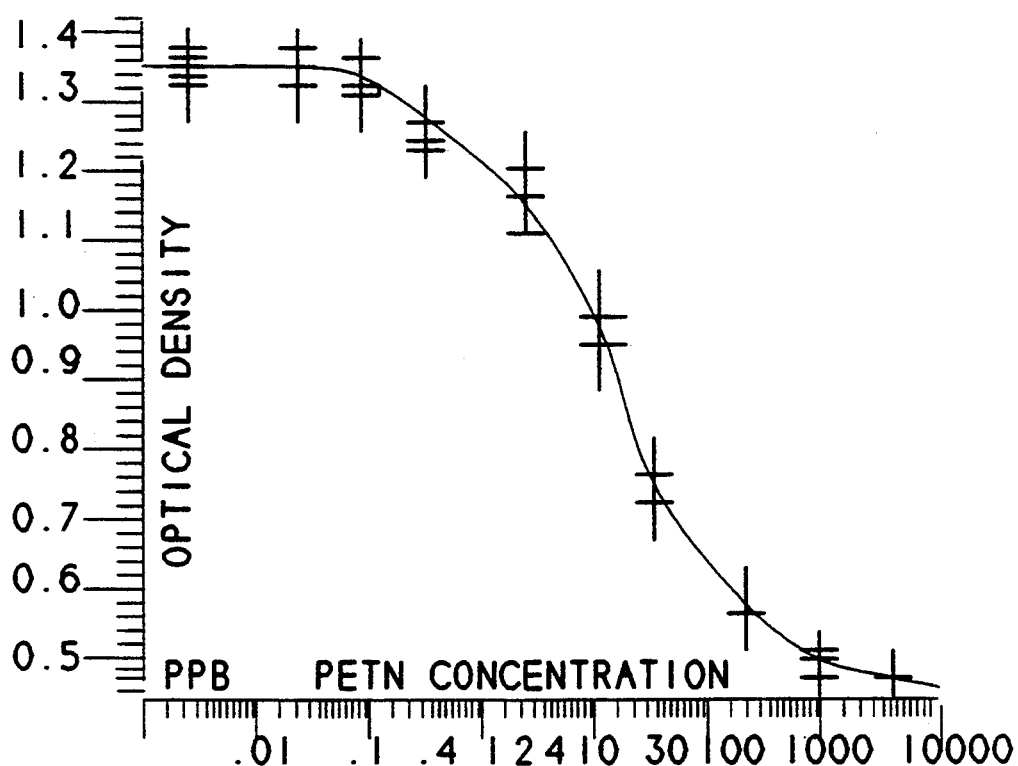
FIG. 2 is a computer generated curve showing optical density of a solution of tetramethylbenzidine in the presence of various concentrations of pentaerythritol tetranitrate.

A 96 well microtiter plate was precoated with 100 microliters of an optimal concentration of PETN-BSA dissolved in PBS and allowed to stand at 4° C. for 18 hours. Known concentrations of antibodies obtained from rabbits immunized with PETN-thyroglobulin were incubated in the precoated wells of the plate for one hour with various concentrations of PETN and NG. The plate washed with PBS to remove all nitrate ester/antibody reaction product from the microtiter plate leaving behind only antibodies bound to the antigen coated on the surface of the wells of the microtiter plate. A goat-anti-rabbit antibody/horse radish peroxidase complex was incubated in the well for 30 minutes to react with the antibodies bound to the microtiter plate. Following a second rinsing to remove unreacted antibody/enzyme complex, a solution of tetramethylbenzidine (TMB) in water was added. After 30 minutes exposure to the TMB, optical density readings were taken on all samples and also on a control sample of the antibody which had not been incubated with either PETN or NG using an automated spectrophotometer to generate the calibration curves shown in FIGS. 1 and 2.

The data obtained indicate a high antibody sensitivity toward both PETN and NG as shown in the following table.

TABLE

| SAMPLE | MINIMUM DETECTABLE LEVEL |
| --- | --- |
| NG | 0.10 parts per billion |
| PETN | 0.03 parts per billion |

It will be apparent to those skilled in the art that various modifications and variations can be made in the processes and products of this invention. Thus it is intended that the invention cover such modifications and variations as fall within the scope of the appended and equivalent claims.

What is claimed is:

1. An antigen for inducing, in a warm blooded mammal, the production of nitrate ester-specific antibodies, which antigen comprises pentaerythritol trinitrate coupled to a carrier protein selected from Bovine Serum Albumin and thyroglobulin via an alkyl carboxy linking group.

2. An antigen according to claim 1 wherein the alkyl carboxy linking group is glutaric acid.

3. An antigen according to claim 2 wherein the protein is Bovine Serum Albumin.

4. An antigen according to claim 2 wherein the protein is thyroglobulin.

* * * * *